United States Patent
Koepnick et al.

(10) Patent No.: US 12,076,178 B2
(45) Date of Patent: Sep. 3, 2024

(54) DEVICE TO CORRECT BACKSCATTER IN X-RAY IMAGES

(71) Applicant: KONINKLIJKE PHILIPS N.V., Eindhoven (NL)

(72) Inventors: Johannes Koepnick, Neumünster (DE); Hanns-Ingo Maack, Noederstedt (DE); Eugen Hermann, Hamburg (DE); Bernd Kuhrmann, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 332 days.

(21) Appl. No.: 17/767,184

(22) PCT Filed: Sep. 25, 2020

(86) PCT No.: PCT/EP2020/076860
§ 371 (c)(1),
(2) Date: Apr. 7, 2022

(87) PCT Pub. No.: WO2021/069237
PCT Pub. Date: Apr. 15, 2021

(65) Prior Publication Data
US 2022/0361836 A1    Nov. 17, 2022

(30) Foreign Application Priority Data

Oct. 10, 2019  (EP) ..................... 19202424

(51) Int. Cl.
  *A61B 6/00*  (2024.01)
  *A61B 6/42*  (2024.01)
  *A61B 6/58*  (2024.01)
(52) U.S. Cl.
  CPC .......... *A61B 6/5282* (2013.01); *A61B 6/4291* (2013.01); *A61B 6/585* (2013.01)

(58) Field of Classification Search
  CPC ...... A61B 6/5282; A61B 6/4291; A61B 6/585
  See application file for complete search history.

(56) References Cited

U.S. PATENT DOCUMENTS

| | | |
|---|---|---|
| 6,548,815 B1 | 4/2003 | Umazaki |
| 9,615,808 B2 | 4/2017 | Mentrup |

(Continued)

FOREIGN PATENT DOCUMENTS

| | | |
|---|---|---|
| WO | WO2015091540 A1 | 6/2015 |
| WO | WO2019011832 A1 | 1/2019 |

OTHER PUBLICATIONS

PCT International Search Report, International application No. PCT/EP2020/076860, Nov. 25, 2020.

*Primary Examiner* — David P Porta
*Assistant Examiner* — Casey Bryant
(74) *Attorney, Agent, or Firm* — Larry Liberchuk

(57) ABSTRACT

An X-ray imaging detector (102) is proposed, wherein the X-ray imaging detector comprises an X-ray converter (103) for converting X-ray radiation into electrical charges. The X-ray imaging detector further comprises a detector plate (104) for collecting the electrical charges generated by the X-ray converter and for generating an image. In addition, the X-ray imaging detector comprises a structured plate (105) for modulating the intensity of backscattered X-ray radiation, wherein the structured plate is arranged at a side of the detector plate opposite the side of the X-ray converter. Moreover, the X-ray imaging detector comprises a data processing system, which is configured for mitigating image distortions caused by backscattered X-ray radiation. Thereto, the data processing system uses information about the structured plate.

15 Claims, 3 Drawing Sheets

(56) References Cited

U.S. PATENT DOCUMENTS

| | | |
|---|---|---|
| 10,918,352 B2 * | 2/2021 | Maack .................. A61B 6/484 |
| 2002/0011572 A1 | 1/2002 | Kajiwara |
| 2017/0296131 A1 * | 10/2017 | Bernhardt ............ A61B 6/5252 |
| 2018/0019035 A1 | 1/2018 | Baturin |
| 2018/0344267 A1 | 12/2018 | Kim |
| 2019/0025443 A1 * | 1/2019 | Minnigh ........... H01M 10/0436 |

* cited by examiner

DEVICE TO CORRECT BACKSCATTER IN X-RAY IMAGES

FIELD OF THE INVENTION

The invention relates to an X-ray imaging detector and an X-ray imaging system. The X-ray imaging detector comprises a structured plate for modulating an intensity of backscattered X-ray radiation and a data processing system for removing image distortions caused by backscattered X-ray radiation.

BACKGROUND OF THE INVENTION

X-ray imaging systems are utilized in a number of applications such as medical diagnostics, airport security, material analysis and others. For example, in medical applications, an X-ray tube and an X-ray imaging detector are arranged on opposite sides of a patient. The X-ray tube may generate a fan beam of X-rays. The photons of the X-ray beam are partially absorbed by the patient's body. Thereby, bones absorb more photons as compared to lean tissue. The photons passing through the patient's body are then received by the X-ray imaging detector, which generates a shadow image of the patient's anatomy. The resulting image is a two-dimensional projection of the three-dimensional structure of the patient's body.

The X-ray imaging detector may comprise an X-ray converter and a detector plate. The X-ray converter converts X-ray radiation into electrical charges. This conversion may be direct or indirect. For example, amorphous selenium may be used for converting X-ray radiation directly into electrical charges. Alternatively, an indirect detector may comprise a scintillator to convert X-ray radiation into visible light, which may then be converted into electrical charges by means of photodiodes. The electrical charges generated by the X-ray converter may be collected by the detector plate. Thereto, the detector plate may comprise an array such as a uniform rectangular array of thin film transistors (TFTs). For example, each TFT may be connected to a photodiode for collecting the charges generated by this photodiode. The detector plate may further comprise readout electronics to read out the electrical charges. These readout electronics may further be configured to convert the electrical charges into pixel values, wherein each pixel value is a single number that represents the electrical charge collected at the corresponding TFT. As a result, the detector plate may generate a digital image comprising the pixel values.

The X-ray converter and the detector plate may absorb around 75% of the impinging X-ray radiation. The remaining 25% of the impinging X-ray photons may propagate through the X-ray converter and the detector plate. To absorb such X-ray photons, conventional X-ray imaging detectors comprise a protection layer, which is a homogeneous layer of a radiopaque material such as lead.

US 2002/0011572 A1 discloses a radiation image pickup device which comprises an image pickup element for converting radiation into an electric signal and picking up an image of an object.

SUMMARY OF THE INVENTION

The protection layer of conventional X-ray imaging detectors may have a significant weight. The weight of the X-ray imaging detector may be less of a concern for X-ray imaging detectors stored in a Bucky tray, but in particular for portable X-ray imaging detectors, it may be beneficial to reduce the weight. Hence, it may be desirable to provide an improved X-ray imaging detector having a lower weight.

This is achieved by the subject matter of the independent claims, wherein further embodiments are incorporated in the dependent claims and the following description. It should be noted that any feature, element, and/or function of the X-ray imaging detector, as described in the following, equally applies to the X-ray imaging system, as described in the following, and vice versa. By replacing the protection layer with a structured plate the weight of the imaging detector is significantly reduced.

According to the present invention, an X-ray imaging detector is presented. The X-ray imaging detector comprises an X-ray converter for converting X-ray radiation into electrical charges, a detector plate for collecting the electrical charges generated by the X-ray converter and for generating an image, a data processing system for processing the image generated by the detector plate, and a structured plate for modulating an intensity of backscattered X-ray radiation, wherein the X-ray converter, the detector plate, and the structured plate are arranged in this order. Namely, the structured plate is arranged at a side of the detector plate opposite the side of the X-ray converter, in other words, the detector plate is sandwiched in between the structured plate and the X-ray converter. Further, the data processing system is configured to remove image distortions caused by the backscattered X-ray radiation using information about the structured plate.

An X-ray tube may emit an X-ray beam. The X-ray photons may propagate, at least in part, through an object to be analyzed. After propagating through this object, the X-ray photons may impinge onto the X-ray converter of the X-ray imaging detector. The X-ray converter may be a direct converter, which may comprise, for example, amorphous selenium for directly converting X-ray radiation into electrical charges. Alternatively, the X-ray converter may be an indirect converter, which may comprise a scintillator and an array of photodiodes. The X-ray converter may convert the impinging X-ray radiation at least in part into electrical charges. For example, the X-ray converter may comprise a uniform rectangular array of X-ray conversion elements, each X-ray conversion element being configured to convert impinging X-ray radiation at least in part into electrical charges. The electrical charges generated by the X-ray converter are collected by the detector plate, which may comprise, for example, a uniform rectangular array of detector elements. Thereto, each detector element may comprise a switch such as a TFT. In particular, each detector element may collect the electrical charges of one X-ray conversion element. The detector plate may further comprise readout electronics for reading out the electrical charges collected by the detector elements. The readout electronics may further be configured to convert the electrical charges into image pixel values. Hence, the detector plate may be configured for generating a digital image representing the amount of X-ray radiation that impinged onto the X-ray imaging detector.

However, a significant portion of the impinging X-ray radiation may propagate through the X-ray converter and the detector plate. This X-ray radiation may impinge onto a structured plate. As defined in claim 1, the X-ray converter, the detector plate and the structured plate are arranged in this order, or in other words the structured plate is arranged at a side of the detector plate opposite the side of the X-ray converter. Hence, the structured plate is arranged behind the detector plate. The X-ray converter, the detector plate, and the structured plate are preferably pairwise parallel to each other. Herein, the direction orthogonal to the structured plate is referred to as the imaging direction. Further, the region "in front of the X-ray converter" is to be understood as the region on the opposite side of the X-ray converter than the detector plate. Moreover, the region "behind the structured plate" is the region on the opposite side of the structured plate than the detector plate.

The structured plate is configured to modulate the intensity of X-ray radiation. In other words, the structured plate may filter the X-ray radiation, wherein different regions of the structured plate provide different degrees of attenuation of X-ray radiation. For example, in some regions of the structured plate, the attenuation of X-ray radiation may be negligible, whereas the attenuation may be significant in other regions of the structured plate. However, even the strongest attenuation of X-ray radiation provided by the structured plate may be substantially weaker as compared to the attenuation provided by conventional X-ray protection layers. For example, conventional X-ray protection layers may attenuate X-ray radiation by 90% or more, meaning that at most 10% of the X-ray photons propagate through conventional X-ray protection layers. In contrast, the strongest attenuation of X-ray radiation provided by the structured plate may be 50% or less. The structured plate may superimpose a spatial pattern onto the intensity of the X-ray radiation that propagated through the X-ray converter and the detector plate.

One or more objects may be located in the region behind the structured plate. These objects may scatter back X-ray radiation, which propagated through the X-ray converter, the detector plate, and the structured plate. Some of these objects may be part of the X-ray imaging detector. For example, the data processing system of the X-ray imaging detector may be arranged in the region behind the structured plate. The X-ray imaging detector may comprise various other components such as a power supply in the region behind the structured plate. Other objects of the environment surrounding the X-ray imaging detector may also scatter back X-ray radiation. For example, the X-ray imaging detector may lie on top of a table, which may scatter back X-ray radiation.

Backscattered X-ray photons may propagate again through the structured plate and the detector plate. Upon impinging onto the X-ray converter, the backscattered X-ray photons may generate electrical charges, which may cause image distortions in the image generated by the detector plate. Since the structured plate modulates the intensity of the backscattered X-ray radiation, it may induce a pattern in the image distortions caused by backscattered X-ray radiation. In other words, the image distortions caused by backscattered X-ray radiation may have a structure, which depends on the structured plate and which may be utilized for mitigating or removing these image distortions.

Correspondingly, the X-ray imaging detector comprises a data processing system, which is configured to remove image distortions caused by backscattered X-ray radiation. Thereto, the data processing system uses information about the structured plate. For example, the data processing system may utilize a calibration image of the structured plate, i.e., an image of the structured plate that has been recorded in a calibration mode. In particular, the calibration image may have been recorded in the absence of another object to be analyzed by means of X-ray radiation. Additionally or alternatively, the data processing system may utilize other kinds of information about the structured plate such as a theoretical model describing its structure. For example, the structured plate may comprise a uniform rectangular array of radiopaque portions embedded in a radiolucent material. In this case, information about the locations and sizes of the radiopaque portions may be provided, and this information may be utilized by the data processing system for removing image distortions caused by the backscattered X-ray radiation.

Methods for mitigating structured image distortions using information about a superimposed pattern have been described previously, see e.g. EP 3490455 A1.

In an example, the structured plate comprises radiopaque portions and radiolucent portions.

In order to modulate the intensity of backscattered X-ray radiation, the structured plate may comprise radiopaque portions and radiolucent portions, wherein the radiopaque portions provide a stronger attenuation of X-ray radiation than the radiolucent portions. The radiopaque portions may be separated by radiolucent portions of the structured plate, or the radiopaque portions may be connected to each other. Similarly, radiolucent portions may be separated by radiopaque portions of the structured plate, or the radiolucent portions may be connected to each other.

The radiopaque portions may comprise a radiopaque material. The radiopaque material may be a chemical element of the fourth or higher periods of the periodic table of elements. Alternatively, the radiopaque material may be a compound or an alloy comprising atoms of the fourth or higher periods of the periodic table of elements. In particular, the radiopaque portions may comprise lead, tungsten, molybdenum, or gold. Other radiopaque materials are possible.

The radiolucent portions may comprise a radiolucent material. The radiolucent material may be a chemical element with an atomic number smaller than 15. Alternatively, the radiolucent material may be a compound or an alloy comprising atoms with atomic numbers smaller than 15. In particular, the radiolucent portions may comprise air, carbon, aluminum, paper, or plastic. Other radiolucent materials are possible.

In another example, the radiopaque portions are configured to have a minimum extent in a direction parallel to the structured plate that is larger than a size of gaps between adjacent conversion elements of the X-ray converter.

In other words, for all directions parallel to the structured plate, the extent of the radiopaque portions is larger than the size of gaps between adjacent conversion elements of the X-ray converter. For the sake of brevity, the minimum extent of the radiopaque portions in a direction parallel to the structured plate is hereafter referred to as the width of the radiopaque portions. Similarly, the minimum extent of the radiolucent portions in a direction parallel to the structured plate is hereafter referred to as the width of the radiolucent portions.

By ensuring that the width of the radiopaque portions is larger than the size of gaps between adjacent conversion elements, it may be ensured that the radiopaque portions do not fully overlap with regions of the X-ray converter, which are insensitive to X-ray radiation. Hence, it may be ensured that the radiopaque portions are visible at least partially in the image generated by the detector plate. In other words, it may be ensured that the structured plate induces a pattern in the image distortions caused by backscattered X-ray radiation. Information about this pattern or corresponding information about the structured plate may be used by the data processing system for removing image distortions caused by backscattered X-ray radiation.

In another example, the minimum extent of the radiopaque and/or radiolucent portions in a direction parallel to the structured plate is at least 1 mm.

The structured plate is configured to superimpose a pattern onto the backscattered X-ray radiation. This pattern can be rather coarse. In particular, the width of the radiopaque portions can be 1 mm or larger. The radiopaque portions can have a large width especially when these portions provide a strong attenuation of X-ray radiation such as 70%, 80%, or larger. Additionally or alternatively, the radiopaque portions can have a large width when spatial variations of the backscattered X-ray intensity are smooth, i.e., when objects behind the structured plate do not cause sharp variations of the backscattered X-ray intensity.

Similarly, the width of the radiolucent portions can be 1 mm or larger. In particular, the radiolucent portions can have a large width when spatial variations of the backscattered X-ray intensity are smooth.

In another example, the radiopaque portions of the structured plate comprise lead, and the extent of the radiopaque portions in a direction perpendicular to the structured plate is 0.05 mm to 0.2 mm.

The extent of the radiopaque portions in the direction perpendicular to the structured plate may be configured to provide a certain attenuation of backscattered X-ray radiation that propagates through the radiopaque portions. The extent of the radiopaque portions in the direction perpendicular to the structured plate is hereafter briefly referred to as the thickness of the radiopaque portions. This thickness is preferably configured to provide an attenuation of 20% to 70% of the backscattered X-ray radiation that propagates through the radiopaque portions. Stronger attenuations of the backscattered X-ray radiation are also possible.

The attenuation provided by the radiopaque portions depends on their thickness and the attenuation coefficient of the material of the radiopaque portions. Thereby, the attenuation coefficient may account for absorption and scattering, including coherent scattering. The attenuation coefficient depends on the frequency of the X-ray radiation and on the material. Hence, different thicknesses of the radiopaque portions may be configured for different radiopaque materials and for different frequencies of the X-ray radiation.

For example, the attenuation coefficient of lead for a frequency corresponding to photon energies of 100 keV is about $\mu=6/mm$. Hence, a radiopaque portion made of lead with a thickness of $d=0.1$ mm provides an attenuation of $1-\exp(-\mu d)=45\%$. More generally, the thickness of radiopaque portions comprising lead may be 0.05 mm to 0.2 mm.

The radiopaque portions of the structured plate may comprise other materials than lead. For example, the radiopaque portions may comprise tungsten, molybdenum, or gold. For such materials, different thicknesses of the radiopaque portions may be configured.

It follows from the above explanations that the width of the radiolucent portions may be larger than the thickness of the radiopaque portions. Values of the width of the radiolucent portions and the thickness of the radiopaque portions may vary significantly, but the width of the radiolucent portions may typically range from a value of 0.2 times the thickness of the radiopaque portions to 50 times the thickness of the radiopaque portions. For example, the width of the radiolucent portions may be 0.2, 0.4, 1, 2, 4, 10, 20 or 50 times the thickness of the radiopaque portions.

In another example, an extent of the radiopaque portions in a direction perpendicular to the structured plate is configured such that X-ray radiation is attenuated by 50% or less when propagating through the radiopaque portions.

An objective of the present invention is to reduce the weight of the X-ray imaging detector. The radiopaque portions of the structured plate may comprise a dense material, so these portions may contribute significantly to the weight of the structured plate. For this reason, the thickness of the structured plate and in particular the thickness of the radiopaque portions should preferably be small.

The structured plate is configured to modulate the intensity of the backscattered X-ray radiation. Hence, the structured plate is configured to superimpose a pattern onto image distortions caused by backscattered X-ray radiation. The data processing system may be configured to determine a first pixel of the image generated by the detector plate, wherein the first pixel corresponds to a radiopaque portion of the structured plate. In other words, backscattered X-ray radiation, which propagated through a radiopaque portion of the structured plate, may contribute to the value of the first pixel. Similarly, the data processing system may be configured to determine a second pixel, wherein the second pixel corresponds to a radiolucent portion of the structured plate. Thus, backscattered X-ray radiation, which did not propagate through a radiopaque portion of the structured plate, may contribute to the second pixel. The data processing system may be configured to remove image distortions in the first and second pixels caused by backscattered X-ray radiation based on the values of the first and second pixels and based on information about the attenuation provided by the radiopaque portions of the structured plate.

Radiopaque portions may be configured to provide an attenuation of the backscattered X-ray radiation such that the impact of this attenuation onto pixel values is well-above quantization errors induced by the read-out electronics. However, it may be sufficient when radiopaque portions of the structured plate attenuate the backscattered X-ray radiation by 20%, 30%, 40%, 50%, 60%, or 70%.

In another example, the weight of the structured plate is less than 200 g.

In another example, the radiopaque portions comprise radiopaque spheres and/or ellipsoids embedded in a radiolucent material, or the radiolucent portions comprise radiolucent spheres and/or ellipsoids embedded in a radiopaque material.

In other examples, radiopaque spheres and/or ellipsoids may be arranged on the surface of a radiolucent layer. The radiopaque portions may also comprise other shapes such as cuboids. Similarly, radiolucent spheres and/or ellipsoids may be arranged on the surface of a radiopaque layer, and/or the radiolucent portions may have shapes other than spheres or ellipsoids.

The material of the radiopaque portions may have a higher density than the material of the radiolucent portions. A structured plate comprising radiopaque spheres embedded in or arranged on a radiolucent layer may have a particularly low weight.

In another example, the radiopaque portions comprise radiopaque cylinders and/or bars separated by the radiolucent portions, or the radiolucent portions comprise radiolucent cylinders and/or bars separated by the radiopaque portions.

The radiopaque or radiolucent cylinders may be oriented orthogonal to the structured plate. Hence, the axes of the cylinders may be parallel to the imaging direction. The cylinders may penetrate the structured plate partially or fully.

Cross-sections of the cylinders in planes parallel to the structured plate may be circular or elliptic. Other cross-sections of the cylinders in planes parallel to the structured plate are also possible. In some examples, the cylinders may be oblique cylinders.

Alternatively, the structured plate may comprise radiopaque or radiolucent bars, which may be oriented parallel to the structured plate. The length of the bars may be equal to the corresponding dimension of the structured plate. Alternatively, the length of the bars may be a fraction of the corresponding dimension of the structured plate. For example, a plurality of radiopaque bars may be arranged along a line with radiolucent portions in between. Similarly, a plurality of radiolucent bars may be arranged along a line with radiopaque portions in between.

In another example, the radiopaque or radiolucent portions are distributed and/or oriented irregularly.

The pattern superimposed by the structured plate onto the image distortions caused by backscattered X-ray radiation should be non-similar to patterns of the object to be analyzed. Furthermore, the pattern superimposed by the structured plate onto the image distortions caused by backscattered X-ray radiation should be non-similar as compared to X-ray intensity patterns induced by the backscattering objects in the region behind the structured plate. Moreover, the pattern superimposed by the structured plate onto the image distortions caused by backscattered X-ray radiation should be non-similar as compared to X-ray intensity patterns induced by other objects, which may absorb backscattered X-ray radiation, and/or which may be located in the region behind the structured plate. This may be achieved by distributing the radiopaque or radiolucent portions irregularly in the structured plate. For example, the radiopaque or radiolucent portions may be distributed randomly in the structured plate. Additionally or alternatively, the radiopaque or radiolucent portions may be oriented randomly.

A random distribution of radiopaque and radiolucent portions in the structure plate may also facilitate and a time and/or cost-efficient manufacturing of the structured plate.

In another example, the radiopaque or radiolucent portions form a regular stripe pattern or a regular grid.

For example, the structured plate may comprise a radiopaque layer with parallel radiopaque bars attached to this layer. The interspaces between the radiopaque bars may be filled with a radiolucent material to form the radiolucent portions. The radiolucent material may be air or another gas. Alternatively, the radiolucent material may be aluminum, carbon, or another solid-state material. The radiopaque layer may be dispensable, i.e., radiopaque and radiolucent bars may be stacked to form the structured plate. Alternatively, the structured plate may comprise a radiolucent layer with parallel radiolucent bars attached to this layer. The interspaces between the radiolucent bars may be filled with a radiopaque material to form the radiopaque portions.

Alternatively, the radiopaque or radiolucent portions may form a regular grid such as a rectangular or hexagonal grid.

Bars of the regular stripe pattern or the regular grid may be parallel to the rows or columns of detector elements of the detector plate. Alternatively, bars of the regular stripe patter or the regular grid may be angled relative to the rows and columns of the detector elements of the detector plate.

In another example, the spatial frequency of the radiopaque portions is higher in a first region of the structured plate than in a second region of the structured plate.

For example, the image generated by the detector plate may have a first section, which may usually be more relevant than a second section of the image. For example, the center of the image may often be more relevant than the edges of the image. The first and second sections of the image generated by the detector plate may correspond, respectively, to the first and second regions of the structured plate.

In the first region of the structured plate, the spatial frequency of the radiopaque portions may be higher than in the second region of the structured plate. The higher spatial frequency of the radiopaque portions in the first region of the structured plate may allow to achieve a better contrast in the corresponding first section of the image generated by the detector plate. At the same time, a higher spatial frequency of the radiopaque portions may result in a higher weight of the structured plate, since the radiopaque material of the radiopaque portions may have a higher density than the radiolucent material of the radiolucent portions. Thus, by configuring a lower spatial frequency of the radiopaque portions in the second region of the structured plate than in the first region of the structured plate, the weight of the structured plate may be reduced.

In another example, the X-ray imaging detector further comprises a component, which induces backscattered X-ray radiation with sharp intensity variations in the first region of the structured plate.

In this case, the structured plate may comprise a higher spatial frequency of radiopaque portions in the first region of the structured plate as compared to a second region of the structured plate. The high spatial resolution of the radiopaque portions in the first region of the structured plate may allow to resolve the backscattered X-ray intensity variations caused by the backscattering component. Thereby, an improved contrast in a corresponding first section of the image generated by the detector plate may be achieved. At the same time, a higher spatial frequency of the radiopaque portions may result in a higher weight of the structured plate, since the material of the radiopaque portions may have a higher density than the material of the radiolucent portions. Thus, by configuring a lower spatial frequency of the radiopaque portions in a second region of the structured plate than in the first region of the structured plate, the weight of the structured plate may be reduced.

In another example, the data processing system is configured to utilize a calibration image of the structured plate for removing the image distortions caused by the backscattered X-ray radiation.

For capturing the calibration image of the structured plate, the X-ray tube may be arranged in the region behind the structured plate, that means the X-ray tube, the structured plate, the detector plate, and the X-ray converter may be arranged in this order. Alternatively, the calibration image of the structured plate may be recorded by arranging the X-ray tube, the structured plate, the X-ray converter, and the detector plate in this order.

According to the present invention, also an X-ray imaging system is presented. The X-ray imaging system comprises an X-ray tube and an X-ray imaging detector according to the present invention.

Furthermore, an object to be analyzed may be arranged between the X-ray tube and the X-ray imaging detector. The X-ray tube may be configured to emit an X-ray beam in the direction of this object. The X-ray beam may partially be attenuated by the object. The X-ray imaging detector may be configured to generate an image representing the intensity of the X-ray radiation after propagation through the object. The structured plate and the data processing system of the X-ray imaging detector are configured to remove image distortions caused by backscattered X-ray radiation from the image generated by the X-ray imaging detector. The X-ray imaging system may further comprise a control unit for synchronizing the operation of the X-ray tube and the X-ray imaging detector, and/or for controlling imaging parameters such as the tube voltage, the tube current, the integration period, etc.

It shall be understood that the X-ray imaging detector and the X-ray imaging system as defined in the claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
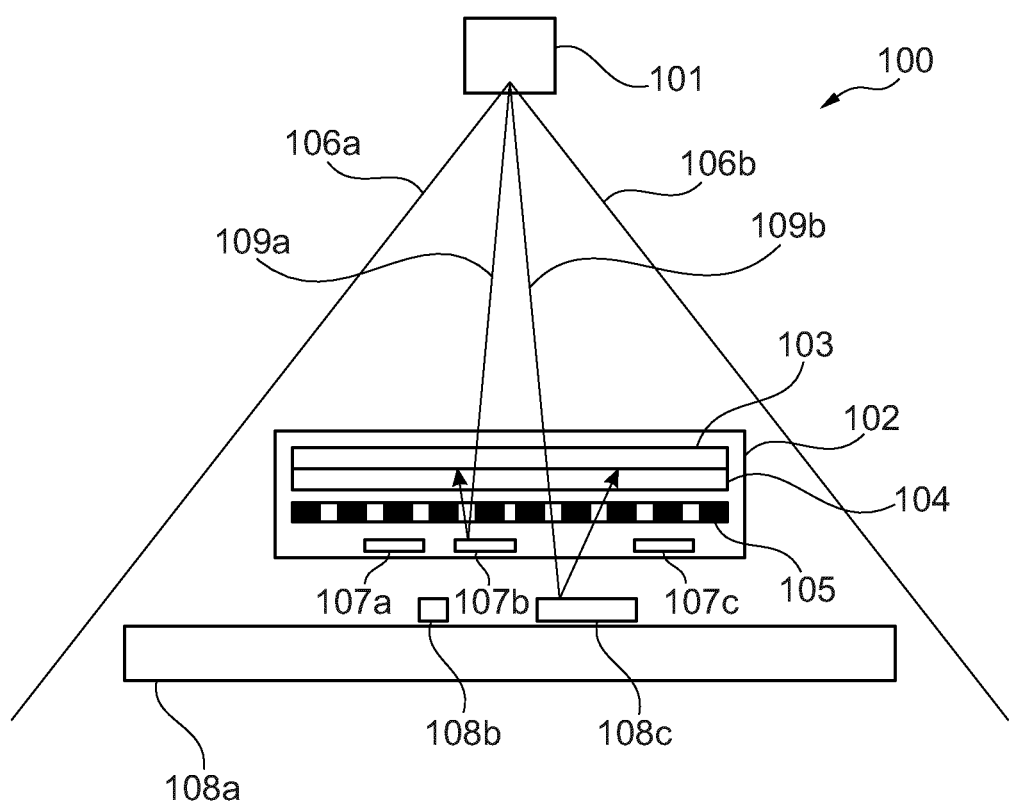
FIG. 1 shows schematically and exemplarily an embodiment of an X-ray imaging system.

FIG. 1 shows schematically and exemplarily an embodiment of an X-ray imaging system 100. The X-ray imaging system comprises an X-ray tube 101 and an X-ray imaging detector 102. The X-ray tube may be configured for emitting an X-ray beam towards the X-ray imaging detector. In FIG. 1, the shape of the X-ray beam is illustrated by outermost X-rays 106a and 106b. An object to be analyzed may be placed in the region between the X-ray tube and the X-ray imaging detector (not shown in FIG. 1).

The X-ray imaging detector comprises an X-ray converter 103 for converting X-ray radiation into electrical charges and a detector plate 104 for collecting the electrical charges generated by the X-ray converter and for generating an image.

The X-ray converter may be a direct or an indirect converter. For example, the X-ray converter may comprise amorphous selenium for directly converting X-ray radiation into electrical charges. Alternatively, the X-ray converter may comprise a scintillator for converting X-ray radiation into light and an array of photodiodes for converting the light into electrical charges. The X-ray converter may comprise an array of conversion elements, each conversion element being configured for converting X-ray radiation into electrical charges.

The detector plate 104 may comprise a corresponding array of detector elements for collecting the electrical charges generated by the conversion elements of the X-ray converter. Thereto, each detector element may comprise a TFT. The detector plate may further comprise readout electronics for reading out an image, wherein each pixel of the image may correspond to the electrical charges generated by one conversion element of the X-ray converter. Hence, the detector plate may be configured for generating a digital image visualizing the amount of X-ray radiation that impinged onto the X-ray converter.

The X-ray converter may attenuate the impinging X-ray radiation by about 75%. The remaining approximately 25% of the X-ray radiation may propagate through the X-ray converter and the detector plate. This X-ray radiation may impinge onto the structured plate 105, which is arranged behind the detector plate when seen from the X-ray converter. The structured plate may be configured for modulating the intensity of X-ray radiation. Thereto, the structured plate may comprise radiopaque and radiolucent portions.

In the region behind the structured plate (when seen from the detector plate), one or more objects may be located, which may scatter back the X-ray radiation that propagated through the X-ray converter, the detector plate, and the structured plate, or that passed those laterally. For example, the X-ray imaging detector may comprise one or more objects 107a, 107b, and 107c, which may scatter back X-ray radiation. Such objects may be components of the data processing system of the X-ray imaging detector or a power supply. FIG. 1 illustrates an X-ray 109a, which propagates from the X-ray tube through the X-ray converter, the detector plate, and the structured plate. The object 107b scatters the X-ray 109a back towards the X-ray converter. Upon impinging onto the X-ray converter, the backscattered X-ray 109a may be converted into electrical charges, which results in a distortion of the image generated by the detector plate 104. Furthermore, FIG. 1 illustrates several objects 108a, 108b, and 108c of the environment of the X-ray imaging system. Such objects may also induce a backscattering of X-ray radiation. For example, FIG. 1 illustrates an X-ray 109b, which propagates through the X-ray converter, the detector plate, and the structured plate. The object 108c scatters the X-ray 109b back towards the X-ray converter, where electrical charges may be generated resulting in a distortion of the image.

The structured plate modulates the intensity of the backscattered X-ray radiation. The image distortions caused by backscattered X-ray radiation therefore have a superimposed pattern, which corresponds to the structure and composition of the structured plate. The data processing system of the X-ray imaging detector may be configured to mitigate the distortions caused by backscattered X-ray radiation. Thereto, the data processing system may utilize information about the structured plate. For example, the data processing system may utilize a calibration image of the structured plate. Additionally or alternatively, the data processing system may use a theoretical model of the structured plate. This theoretical model may comprise information about locations and sizes of radiopaque portions of the structured plate. In addition, the theoretical model may comprise information about attenuations provided by the radiopaque portions.

The pattern superimposed by the structured plate onto the image distortions caused by backscattered X-ray radiation should be non-similar to patterns of the object to be analyzed. Furthermore, the pattern superimposed by the structured plate onto the image distortions caused by backscattered X-ray radiation should be non-similar as compared to X-ray intensity patterns induced by the backscattering objects 107a to 107c and 108a to 108c. Moreover, objects such as 108b or 108c may be absorbing X-ray radiation scattered back by object 108a, thereby inducing X-ray intensity patterns of the backscattered X-ray radiation. The pattern superimposed by the structured plate onto the image distortions caused by backscattered X-ray radiation should also be non-similar as compared to X-ray intensity patterns induced by backscattered X-ray radiation absorbing objects such as 108b or 108c. This may be achieved by distributing the radiopaque or radiolucent portions irregularly in the structured plate. For example, the radiopaque or radiolucent portions may be distributed randomly in the structured plate. Additionally or alternatively, the radiopaque or radiolucent portions may be oriented randomly.

FIGS. 2a to 2e schematically and exemplarily depict embodiments of a structured plate for an X-ray imaging detector. The structured plates of FIGS. 2a to 2e are shown from a viewing direction that is orthogonal to the structured plate.

Figure 2A:
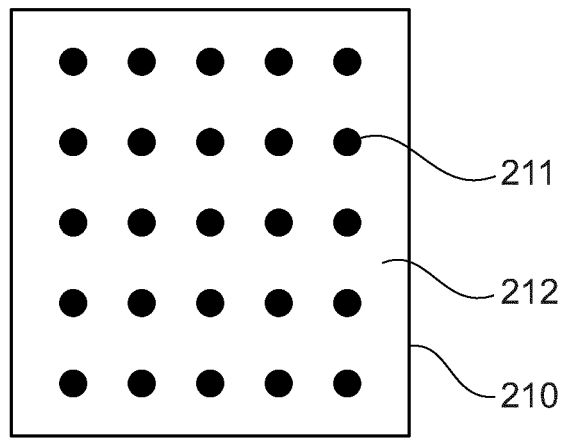
FIGS. 2a to 2e show schematically and exemplarily embodiments of a structured plate of an X-ray imaging detector.

For example, FIG. 2a depicts a structured plate 210 comprising radiopaque portions 211 and radiolucent portions 212. The radiopaque portions are arranged according to a uniform rectangular array. In FIG. 2a, the radiopaque portions may be radiopaque spheres embedded in a radiolucent material. Alternatively, radiopaque spheres may be arranged on the surface of a radiolucent layer. It is also possible, that the radiopaque portions are radiopaque cylinders, which partially or fully penetrate the structured plate. Thereby, the axes of the radiopaque cylinders are orthogonal to the structured plate. Since FIG. 2a represents a two-dimensional visualization of the three-dimensional structured plate, several other variations of the shape of the radiopaque portions can be conceived by the person skilled in the art.

Figure 2B:
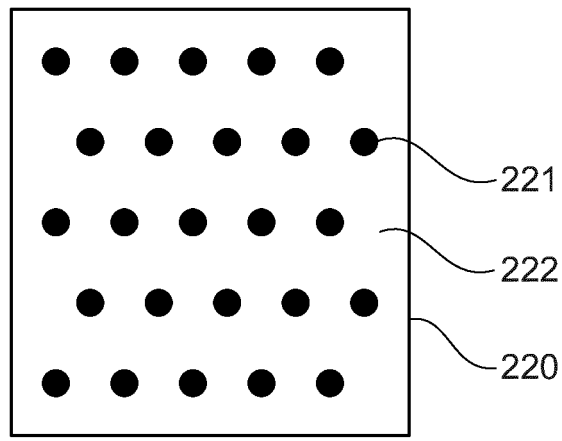

FIG. 2b depicts a similar structured plate 220 with radiopaque portions 221 and radiolucent portions 222. However, the radiopaque portions are arranged in FIG. 2b according to a uniform hexagonal array geometry.

Figure 2C:
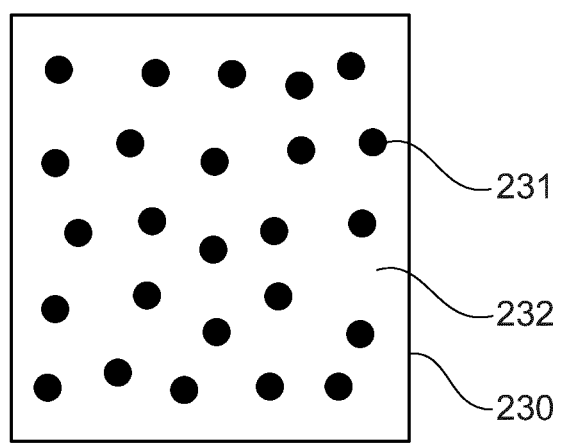

FIG. 2c depicts another structured plate 230 with radiopaque portions 231 and radiolucent portions 232. However, the radiopaque portions 231 are distributed randomly in FIG. 2c.

Figure 2D:
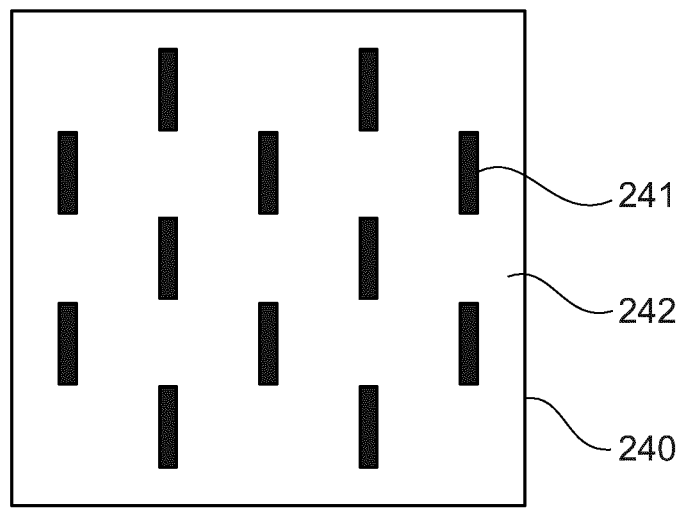

FIG. 2d shows another structured plate 240 with radiopaque portions 241 and radiolucent portions 242. In FIG. 2d, the radiopaque portions are radiopaque bars having a length that is shorter than the corresponding dimension of the structured plate. The bars are arranged in FIG. 2d according to a uniform hexagonal array.

Figure 2E:
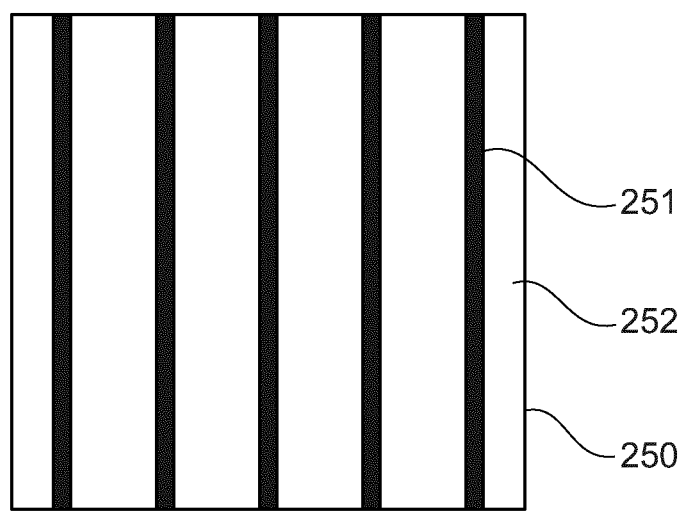

FIG. 2e depicts another structured plate 250 with radiopaque portions 251 and radiolucent portions 252. The structured plate of FIG. 2e comprises a regular stripe pattern of radiopaque bars separated by radiolucent bars.

FIGS. 2a to 2e have been described with radiopaque portions 211, 221, 231, 241, and 251 and with radiolucent portions 212, 222, 232, 242, and 252. The inverse configurations with radiopaque portions 212, 222, 232, 242, and 252 and radiolucent portions 211, 221, 231, 241, and 251 are also possible.

While the invention has been illustrated and described in detail in the drawings and foregoing description, such illustrations and descriptions are to be considered illustrative or exemplary and not restrictive. In particular, the illustrated forms and shapes of the structured plate are only exemplary. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging detector, comprising:
    an X-ray converter for converting X-ray radiation into electrical charges;
    a detector plate for collecting the electrical charges generated by the X-ray converter and for generating an image;
    a data processor configured to process the image generated by the detector plate; and
    a structured plate for modulating an intensity of backscattered X-ray radiation,
    wherein the structured plate is arranged at a side of the detector plate opposite the side of the X-ray converter, and
    wherein the data processor is configured to remove image distortions caused by the backscattered X-ray radiation using information about the structured plate.

2. The X-ray imaging detector of claim 1, wherein the structured plate comprises radiopaque portions and radiolucent portions.

3. The X-ray imaging detector of claim 2, wherein the radiopaque portions are configured to have a minimum extent in a direction parallel to the structured plate that is larger than a size of gaps between adjacent conversion elements of the X-ray converter.

4. The X-ray imaging detector of claim 3, wherein the minimum extent of the radiopaque portions in a direction parallel to the structured plate is at least 1 mm.

5. The X-ray imaging detector of claim 2, wherein the radiopaque portions of the structured plate comprise lead, and wherein an extent of the radiopaque portions in a direction perpendicular to the structured plate is 0.05 mm to 0.2 mm.

6. The X-ray imaging detector of claim 2, wherein an extent of the radiopaque portions in a direction perpendicular to the structured plate is configured such that the X-ray radiation is attenuated by 50% or less when propagating through the radiopaque portions.

7. The X-ray imaging detector of claim 2, wherein the radiopaque portions comprise radiopaque spheres and/or ellipsoids embedded in a radiolucent material, or wherein the radiolucent portions comprise radiolucent spheres and/or ellipsoids embedded in a radiopaque material.

8. The X-ray imaging detector of claim 2, wherein the radiopaque portions comprise radiopaque cylinders and/or bars separated by the radiolucent portions, or wherein the radiolucent portions comprise radiolucent cylinders and/or bars separated by the radiopaque portions.

9. The X-ray imaging detector of claim 2, wherein the radiopaque or radiolucent portions are distributed and/or oriented irregularly.

10. The X-ray imaging detector of claim 2, wherein the radiopaque or radiolucent portions form a regular stripe pattern or a regular grid.

11. The X-ray imaging detector of claim 2, further comprising a component which induces backscattered X-ray radiation with sharp intensity variations in a first region of the structured plate, and wherein a spatial frequency of the radiopaque or radiolucent portions is higher in the first region of the structured plate than in a second region of the structured plate.

12. The X-ray imaging detector of claim 1, wherein a weight of the structured plate is less than 200 g.

13. The X-ray imaging detector of claim 1, wherein the data processor is configured to utilize a calibration image of the structured plate for removing the image distortions caused by the backscattered X-ray radiation.

14. The X-ray imaging detector of claim 2, wherein the radiolucent portions comprise at least one of air, carbon, aluminum, and plastic.

15. An X-ray imaging system, comprising:
an X-ray tube; and
an X-ray imaging detector comprising:
- an X-ray converter for converting X-ray radiation into electrical charges;
- a detector plate for collecting the electrical charges generated by the X-ray converter and for generating an image;
- a data processor configured to process the image generated by the detector plate; and
- a structured plate for modulating an intensity of backscattered X-ray radiation, wherein the structured plate is arranged at a side of the detector plate opposite the side of the X-ray converter, and wherein the data processor is configured to remove image distortions caused by the backscattered X-ray radiation using information about the structured plate.

* * * * *